US011220684B2

(12) United States Patent
Astatke

(10) Patent No.: US 11,220,684 B2
(45) Date of Patent: Jan. 11, 2022

(54) PLATFORM AND METHOD FOR IDENTIFYING PAST EXPOSURE TO CHEMICAL AGENTS OR HEAVY METALS

(71) Applicant: Johns Hopkins University, Baltimore, MD (US)

(72) Inventor: Mekbib Astatke, Gaithersburg, MD (US)

(73) Assignee: The Johns Hopkins University, Baltimore, MD (US)

( * ) Notice: Subject to any disclaimer, the term of this patent is extended or adjusted under 35 U.S.C. 154(b) by 45 days.

(21) Appl. No.: 16/532,020

(22) Filed: Aug. 5, 2019

(65) Prior Publication Data

US 2020/0102552 A1 Apr. 2, 2020

Related U.S. Application Data

(62) Division of application No. 15/249,842, filed on Aug. 29, 2016, now Pat. No. 10,415,032.

(60) Provisional application No. 62/212,617, filed on Sep. 1, 2015.

(51) Int. Cl.
*C12N 15/10* (2006.01)
*C12Q 1/6883* (2018.01)
*G01N 33/68* (2006.01)
*C12Q 1/6804* (2018.01)

(52) U.S. Cl.
CPC ..... *C12N 15/1037* (2013.01); *C12N 15/1065* (2013.01); *C12Q 1/6804* (2013.01); *C12Q 1/6883* (2013.01); *G01N 33/6845* (2013.01); *G01N 2800/42* (2013.01)

(58) Field of Classification Search
CPC ............ C12N 15/1037; C12N 15/1065; C12Q 1/6804; C12Q 1/6883; G01N 33/6845; G01N 2800/42
See application file for complete search history.

(56) References Cited

PUBLICATIONS

Bernard et al. (Clinical chemistry 32.8 (1986): 1468-1472) (Year: 1986).*
Bernard et al. (International archives of occupational and environmental health 59.3 (1987): 303-309.) (Year: 1987).*
Date et al. (Biosensors and Bioelectronics 33 (2012) 106-112) (Year: 2012).*
Waterman et al. (Environmental health perspectives 102.12 (1994): 1052-1056). (Year: 1994).*
Hu, Y. I., et al. "Proteome analysis of *Saccharomyces cerevisiae* under metal stress by two-dimensional differential gel electrophoresis." Electrophoresis 24.9 (2003): 1458-1470. (Year: 2003).*
Elad, Tal, and Shimshon Belkin. "Broad spectrum detection and "barcoding" of water pollutants by a genome-wide bacterial sensor array." Water research 47.11 (2013): 3782-3790. (Year: 2013).*
Bernard et al., "Search for Anti-Laminin Antibodies in the Serum of Workers Exposed to Cadmium, mercury Vapour or Lead," International Archives of Occupational and Environmental health (1987) 59: 303-309.
Bernard et al., "Detection of Anti-Laminin Antibodies in Sera by Latex Agglutination," Clinical Chemistry, vol. 32, No. 8, pp. 1468-1472, 1986.
Larman et al., "Autoantigen Discovery with a Synthetic Human Peptidome," Nature Biotechnology, vol. 29, No. 6, pp. 535-543, Jun. 2011 & supplementary materials, 2011.
Nian et al., "Chromatographic Biopanning for the Selection of Peptides with High Specificity to Pb2+ from Phage Displayed Peptide Library," Journal of Chromatography A, 1217 (2010) 5940-5949.
Date et al., "Microfluidic Heavy Metal Immunoassay Based on Adsorbance Measurement," Biosensors and Bioelectronics, 33 (2012) 106-112.
Hotz et al., "Renal Effects of Low-Level Environmental Cadmium Exposure: 5-Year Follow-up of a Subcohort from the Cadmibel Study," The Lancet, vol. 354, pp. 1508-1513, Oct. 30, 1999.

* cited by examiner

*Primary Examiner* — Sahana S Kaup
(74) *Attorney, Agent, or Firm* — Todd R. Farnsworth

(57) ABSTRACT

A method for determining past exposure to chemical agents or heavy metals may include coating a capture material with a capture reagent. The capture reagent may be selected based on an ability of the capture reagent to bind with a target antibody, and the target antibody may be an indicator associated with a particular chemical agent or heavy metal. The method may further include interrogating a clinical sample associated with an individual by forming a mixture of the capture material and the clinical sample, and determining an exposure status of the individual to the particular chemical agent or heavy metal based on whether the capture material demonstrates capture of the indicator.

9 Claims, 4 Drawing Sheets

PLATFORM AND METHOD FOR IDENTIFYING PAST EXPOSURE TO CHEMICAL AGENTS OR HEAVY METALS

CROSS-REFERENCE TO RELATED APPLICATIONS

This application is a divisional of U.S. patent application Ser. No. 15/249,842, filed on Aug. 29, 2016, which claims the benefit of U.S. Provisional Application No. 62/212,617, filed on Sep. 1, 2015; the entire contents of both are incorporated herein by reference.

STATEMENT OF GOVERNMENTAL INTEREST

This invention was made with Government support under contract number 2012-12050800010 awarded by the Intelligence Advanced Research Projects Activity (IARPA). The Government has certain rights in the invention.

TECHNICAL FIELD

Example embodiments generally relate to technology for detecting past exposure to chemical agents or heavy metals, and more particularly relates to an immunoassay platform and method for the same.

BACKGROUND

Methods have been developed to determine the presence of biomarkers that provide evidence of prior exposure to biological agents. However, for chemical agent exposure, particularly when small levels of exposure occurred or exposure occurred some time ago, there has not typically been any way to determine what exposures have occurred. Furthermore, even for more recent or large level exposures, since chemical agents or heavy metals (ex. Pb) are often too small to be immunogenic, the agents will flush out of an individual's system in a relatively short time and essentially leave no trace to be measured in relatively short period of time. Thus, for example, exposure events are often diagnosed after the fact based on the symptoms experienced by the individual or other public health information, and not based on any positive identification of specific agents/biomarkers found in the individual's system.

More recently, the idea has developed that there may be some way to detect past exposures to chemical agents, or even heavy metals. Recent word events related to intelligence community needs and general public safety concerns have driven continued pursuit of a solution for providing this ability. Accordingly, it may be desirable to develop a method for detecting such past exposures, and perhaps also capable of scanning for multiple different exposures in a single test.

Biomarkers unique to specific agents, chemical or heavy metals that could cause harmful effect on human health are useful for in diagnostic scenarios. Determination of an individual immunomics status by assessing the level of specific immune responses associated with exposures with an array of chemical compounds and their metabolites would significantly enhance our capability to intervene and track deliberate or accidental incidences to chemical agents of interest. Furthermore, subsequent identification of specific modified host peptide sequences that bind to circulating antibodies (Abs) could provide insights into autoimmune diseases and environmental exposures. However, there is an unmet technological gap for specifically determining acute, past and chronic exposures to small chemicals and heavy metals, limiting our ability to pinpoint the mechanism by which these chemicals affect the overall health of the host. Published data suggest that many chemicals covalently attach to host proteins and become haptenized, therefore stimulating the immune system. In addition, a published report indicates that mice exposed to lead produce a specific immune response against 2 altered neural proteins. Generating in vitro all possible adducts with host proteome that could form as a result of chemical exposure event or all possible altered host protein that could result by exposure to heavy metals would greatly enhance our capability to identify host immune response biomarkers in clinical serum samples. The subsequent Abs directed against these chemical adducts and/or altered host proteins via immunoassay techniques would pinpoint the specific peptide adducts or altered peptides that become haptenized.

BRIEF SUMMARY OF SOME EXAMPLES

Accordingly, some example embodiments may enable the provision of a solution for addressing the issues described above. In this regard, for example, some embodiments may enable the provision of a screening platform capable of determining past exposure to one or a plurality of different chemicals, or heavy metals.

In one example embodiment, a method for determining past exposure to chemical agents or heavy metals is provided. The method may include coating a capture material with a capture reagent. The capture reagent may be selected based on an ability of the capture reagent to bind with a target antibody, and the target antibody may be an indicator associated with a particular chemical agent or heavy metal. The method may further include interrogating a clinical sample associated with an individual by forming a mixture of the capture material and the clinical sample, and determining an exposure status of the individual to the particular chemical agent or heavy metal based on whether the capture material demonstrates capture of the indicator.

In another example embodiment, an apparatus for determining past exposure to chemical agents or heavy metals is provided. The apparatus may include a capture material and a test volume. The capture material may be coated with a capture reagent. The capture reagent may be selected based on an ability of the capture reagent to bind with a target antibody. The target antibody may be an indicator associated with a particular chemical agent or heavy metal. The test volume may be a volume in which the capture material is provided for mixture with a clinical sample associated with an individual to interrogate the clinical sample. The apparatus may be configured to provide an output for determining an exposure status of the individual to the particular chemical agent or heavy metal based on whether the capture material demonstrates capture of the indicator.

BRIEF DESCRIPTION OF THE SEVERAL VIEWS OF THE DRAWING(S)

Having thus described example embodiments of the invention in general terms, reference will now be made to the accompanying drawings, which are not necessarily drawn to scale, and wherein:

DETAILED DESCRIPTION

Figure 1:
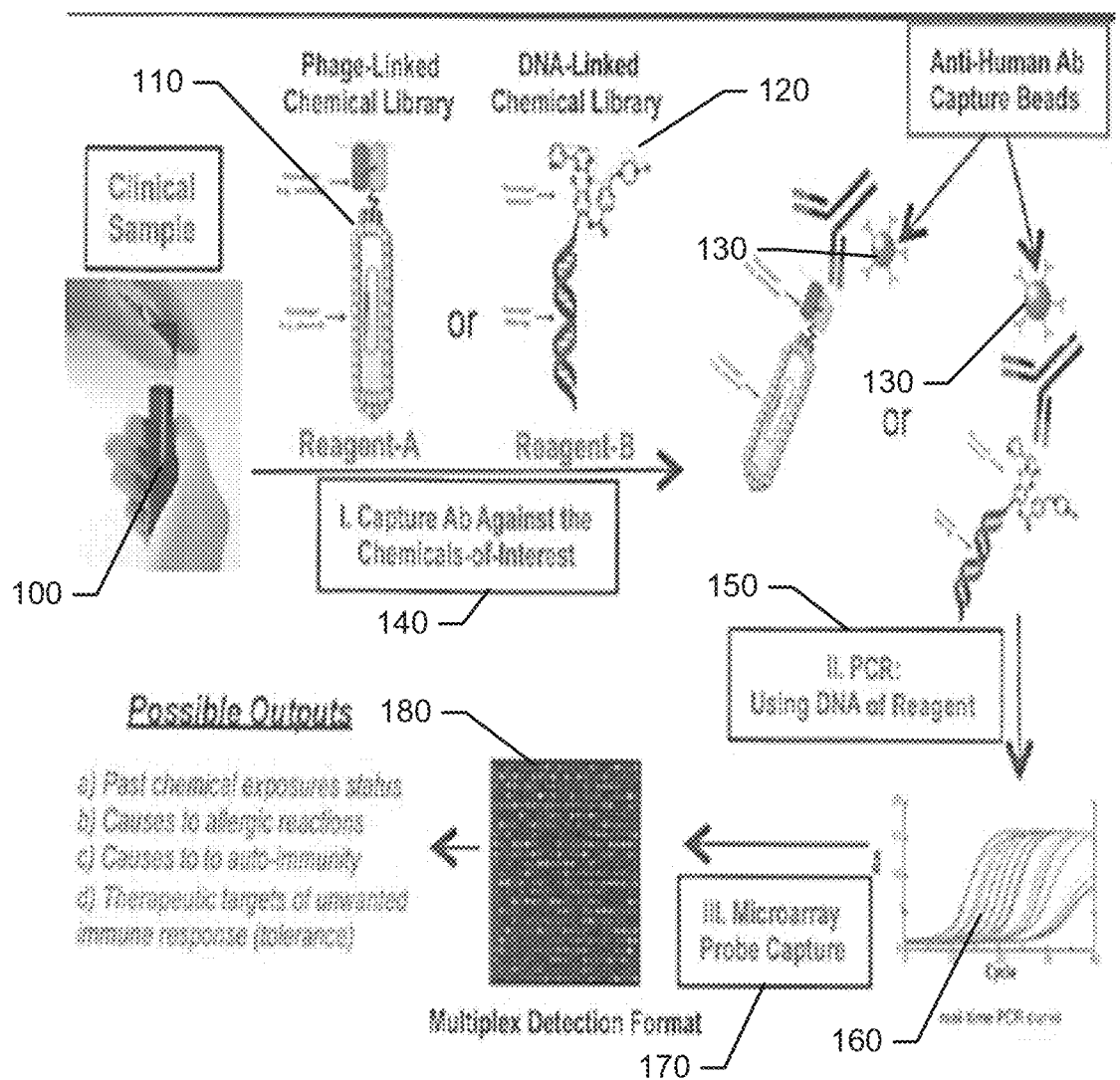
FIG. 1 illustrates a flow diagram to illustrate the operations associated with chemical agent exposure detection in accordance with an example embodiment according to an example embodiment.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

As indicated above, some embodiments of the present invention may relate to providing an exposure screening platform for detecting past chemical or heavy metal (e.g., lead) exposure. Some example embodiments may further allow for multiplexing relative to the screening operation so that the possibility to screen for multiple chemicals or heavy metals is provided. Some examples may employ a chemical-phage library, chemical-DNA library and/or protein modification library for chemicals and heavy metals of interest to enable the capture of antibodies directed at the chemical motifs or modifications. Example embodiments may also be rapidly deployable to respond to public health or intelligence-related incidents to confirm whether exposures have occurred, or may be employed as part of a routine health monitoring program which could develop a timeline for a particular patient or set of patients to determine when exposures may have occurred.

Example embodiments attempt to solve the problem of determining whether an individual has experienced a past exposure to a heavy metal such as lead, or to a chemical agent such as sarin gas, mustard gas, etc. As discussed above, some chemical agents tend to be flushed from the body relatively quickly (e.g., within days) after exposure. Thus, confirmation of exposure can be difficult if testing is not immediately performable. However, some chemical agents may react with various proteins to form protein adducts in blood plasma. The formation of these protein adducts acts somewhat like an immune response, which can act as memory of the exposure event. This memory, as detectable through the existence of protein adducts, can indicate the existence of the exposure event.

Exposure to heavy metals such as lead may also be detected through a somewhat similar memory process for recording the exposure event. More specifically, although exposure to lead does not form protein adducts in the manner described above, the exposure does modify (i.e., cause structural changes to) biomolecules. The modification that occurs when biomolecules bind with metal ions may generate haptens that induce an immune response. Antibodies against the modification may therefore be detected in an individual as evidence or memory indicative of the exposure event.

In both of the example cases described above (i.e., chemical agent and heavy metal exposure cases), it may be possible to generate a library of indicators that can be searched for to provide evidence of exposure. For example, in some cases, a phage or yeast library that display human peptidome may be provided to generate all possible adducts or modification with minimal bias. The library will be exposed to the chemical or heavy metal to generate all possible modification that would be expected during actual exposure. The library may define a unique identifier sequence tag for each of a plurality of chemicals. When a given peptide is detected, an indication may be provided that a covalent chemical linkage was formed based on exposure to a chemical identified from the phage library. Alternatively or additionally, a DNA library may be provided to identify indicators. For example, a DNA library with unique sequences with primary amine or sulfhydryl moiety at the 5'-end may be provided. For heavy metal exposure detection, a library of modifications that could possibly occur in vivo may be provided.

In an example embodiment, the indicators from the library (e.g., the DNA library, the phage-library, or the modification library) may be used to interrogate clinical samples (e.g., of blood, sera, or other suitable bodily fluids) to determine if any antibody against a particular modification or protein adducts can be found. If any unique antibody is found that binds only to a particular entry in the library (e.g., a particular modified biomolecules, a particular protein adduct, etc.), then the corresponding implication is that the sample was derived from an individual that has been exposed to the metal ion or chemical agent associated with the indicator that was detected.

FIG. 1 illustrates a flow diagram to illustrate the operations associated with chemical agent exposure detection in accordance with an example embodiment. In this regard, as shown in FIG. 1, a clinical sample 100 (e.g., blood, sera, or other bodily fluid) may be provided from an individual whose potential exposure to selected chemical agents is to be tested. Using the aforementioned phage/yeast library adduct reagents, all host peptide adducts to each chemical of interest or altered host biomolecule that correspond to each heavy metal that become haptenized to illicit immune response could be identified. Based on this information, a peptide-adduct array sensor will be developed and will be coated as capture molecules. A plurality of reagents corresponding to chemical agents (i.e., capable of binding with antibodies generated by such chemical agents) may be defined in respective ones of a phage-linked chemical library 110 or a DNA-linked chemical library 120. The reagents may correspond to chemicals of interest for testing purposes. Based on the known antibodies that would be generated responsive to exposure to various chemicals (as further provided by information that may be in the libraries), capture beads or some other capturing reagent 130 may be provided to bind to antibodies (if any) in the clinical sample 100. This process may correspond to the capture block 140 of FIG. 1.

After the clinical sample 100 is exposed to the capturing reagent 130, a determination may be made as to whether antibodies were captured, thereby indicating that the individual has been exposed to the corresponding chemical agent. In the case of the DNA-linked library, polymerase chain reaction (PCR) may be used to facilitate enhancing diagnostic sensitivity by coupling antibody detection with DNA tags that can be exponentially amplified. As such, in this example, the PCR block 150 corresponds to an amplification or sensitivity enhancement step. A real-time PCR curve 160 may be generated to show the results of the amplification operations.

Given that multiple capturing reagents may be defined for multiple corresponding chemicals to permit multiplexing relative to the sensor platforms exposure detection capabilities, a microarray probe capture operation 170 may be employed to display the results in a multiplex detection format 180. The multiplex detection format 170 may illustrate results for each of a plurality of detection cells that are generated based on corresponding different capturing reagents that are exposed to the clinical sample 100.

As can be seen from FIG. 1, this procedure can be used to detect past chemical exposure status. The procedure could also be used to determine causes for allergic reactions or auto-immunity responses. In some cases, the procedure could provide an output for therapeutic targets of unwanted immune response (e.g., tolerance). Example embodiments may also be used by the intelligence community to determine exposure status for individuals or populations. In some cases, routine monitoring of individuals (e.g., service members, healthcare workers, special operations forces, etc.) may indicate populations that are sensitized to a set of chemicals that could limit their deployability or involvement in certain missions.

In some cases, the procedure could be adapted to determine a level of circulating antibody specific to a chemical composition as a function of level, duration, chronicity and/or last event of exposure. In this regard, for example, the libraries may further include information to relate particular level measurements, combinations of indicator levels, or patterns of decay of level measurements for a series of tests performed over a period of time, correlate to an indication of an amount of exposure, a time since exposure, a duration of exposure, or how many exposure incidents have occurred for a particular individual. This information may be derived, for example, based on statistical analysis of patient data for larger sets of historical data.

Figure 2:
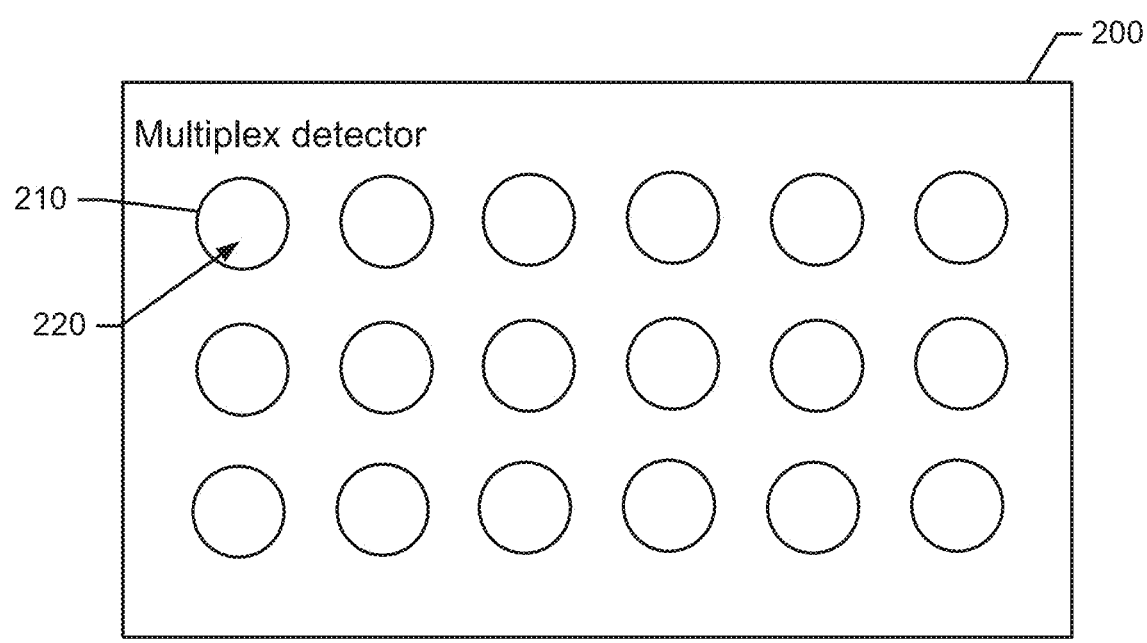
FIG. 2 illustrates a block diagram showing operations an apparatus for performing exposure detection relative to chemical agents and/or heavy metals according to an example embodiment.

FIG. 2 illustrates an apparatus 200 for determining past exposure to chemical agents or heavy metals. The apparatus 200 may be a multiplex detector since it is configured to enable exposure testing to be conducted for a plurality of different chemical agents and/or heavy metals. The detector may include a plurality of test volumes or cells 210 inside which a mixture 220 can be formed including a capture reagent and a clinical sample. Each cell 210 may have a different capture reagent provided therein. Moreover, the capture reagent may be coated or otherwise provided on a capture material (e.g., a capture bead or other structure). The capture reagent may be selected based on an ability of the capture reagent to bind with a target antibody. The target antibody may therefore act as an indicator associated with a particular chemical agent or heavy metal.

As discussed above, in the case of chemical agents, the target antibody may attach to protein adducts formed when exposure to the chemical agent occurs in vivo. For heavy metals, the target antibody may attach to modified biomolecules that were modified by exposure to heavy metals. In any case, a phage library, DNA library, or modification library may be used to define a plurality of known modifications or protein adducts that form based on exposure (in vivo) to corresponding heavy metals or chemical agents, respectively. Thus, each cell 210 may be provided with a different capture material to bind with antibodies (if any are present) that would be expected to form if exposure to the corresponding heavy metal or chemical agent has occurred.

After the clinical sample is mixed with the capture reagent, the mixture may be incubated. Thereafter, unbound reagent may be removed by washing with a suitable solution. After unbound reagent has been removed, specific binding events that have occurred can be determined. Of course, these binding events are indicative of the antibodies that were present in the clinical sample, and therefore indicative of exposure to the corresponding heavy metals or chemical agents defined in the corresponding library. In an example embodiment, a PCR assay may be performed to amplify the results and provide a clearer indication of the binding events that occurred. Thereafter, in some cases, it may be desirable to determine assay sensitivity and specificity for each analog.

Results of the determinations of binding events may be provided in a multiplex detection format (e.g., format 180) that shows information about which cells 210 (if any) had positive indications of exposure events. In some cases, the detection format may further provide information about levels detected (i.e., the amount of antibody captured for the corresponding chemical-of interest or metal-of-interest). Whether the results merely show binary results (i.e., positive or negative results for past exposure to the chemical-of interest or metal-of-interest) or actually provide information indicative of a level or degree of antibody capture events, the results may be displayed in real time, or may be stored for future analysis.

Figure 3:
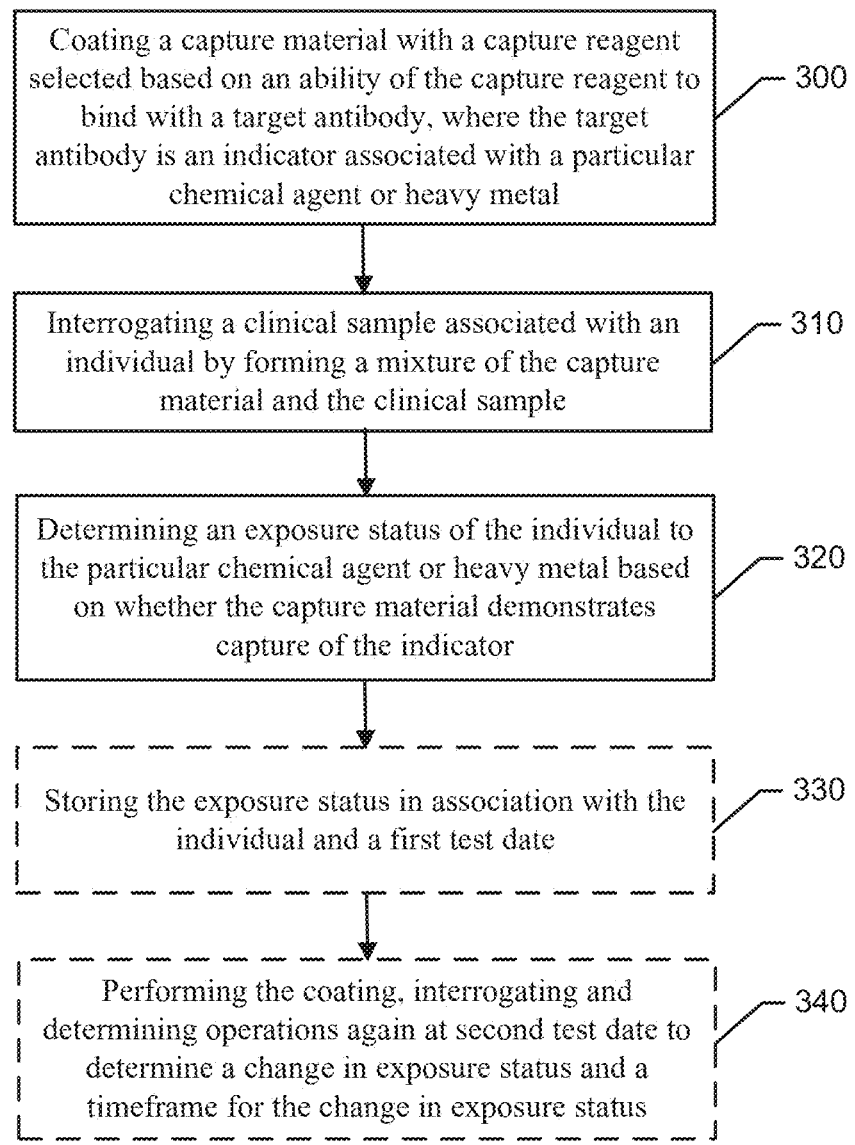
FIG. 3 illustrates a block diagram showing operations associated with a method of detecting exposure events according to an example embodiment.

FIG. 3 illustrates a block diagram of a method of determining past exposure to chemical agents or heavy metals in accordance with an example embodiment. The method may include coating a capture material with a capture reagent at operation 300. The capture reagent may be selected based on an ability of the capture reagent to bind with a target antibody, and the target antibody may be an indicator associated with a particular chemical agent or heavy metal. The method may further include interrogating a clinical sample associated with an individual by forming a mixture of the capture material and the clinical sample at operation 310, and determining an exposure status of the individual to the particular chemical agent or heavy metal based on whether the capture material demonstrates capture of the indicator at operation 320.

In cases where multiplexing is desired, the capture material in each cell may be coated with a respective different capture reagents. Each of the different capture reagents may be known (e.g., via the libraries) to bind with corresponding different target antibodies to act as respective indicators of exposure to the chemical agents or heavy metals. In an example embodiment, the capture material that is coated with the capture reagent may target bindings identified from a phage library, a DNA library, or a modification library to determine the chemical agents or heavy metals that form corresponding protein adducts or biomolecules modifications to which each of the different target antibodies bind.

In an example embodiment, a determination regarding the exposure status of the individual may be made by washing the mixture to remove unbound reagents. Thereafter, a determination may be made as to the binding events that have occurred in association with capture of the indicators. In some cases, a PCR assay may be performed to enhance the sensitivity of the exposure tests.

In some cases, the method may further include additional (optional) operations. For example, the method may further include storing the exposure status in association with the individual and a first test date at operation 330, and performing the coating, interrogating and determining operations again at second test date to determine a change in exposure status and a timeframe for the change in exposure status at operation 330. The operations 300 to 320 may be repeated again and again at various intervals to provide a timeline that may indicate exposure event information for an individual over time. The timeline may enable determinations of when exposure events occur for the individual and, in some cases, whether chronic exposure, multiple discrete exposure events, a single exposure event, magnitude of exposure. In this regard, for example, the first test date may form a baseline measurement in terms of identifying any chemical agents or heavy metals to which the individual has been exposed. An indication of magnitude of the exposure may also be provided by level measurements associated with the first test date.

The first test date may also, by negation, establish a number of tested chemical agents and heavy metals to which the individual has apparently not been exposed as of the first test date. Accordingly, if exposure occurs after the first test date, the exposure may appear on a subsequent test date (e.g., the second test date) to establish a date range within which the exposure must have occurred. The date range may, for example, correspond to a suspected exposure event, which may be confirmed using testing methods associated with example embodiments.

When level measurement is possible and employed, levels measured at the first test date or at any subsequent test dates may be expected to decrease over time for certain chemicals or metals of interest. However, if levels measured increase slowly or in prompt jumps, other information regarding the frequency or nature of exposure can be determined. For example, if levels slowly increase, such a pattern may be indicative of a chronic (perhaps low level) exposure. Meanwhile, if levels were decreasing, increase in one subsequent test, and then return to decreasing thereafter, the pattern may indicate a past exposure event, and a single subsequent exposure event. Other patterns may indicate other information, which may be determinable by studying temporal and/or level information associated with exposure analysis in accordance with example embodiments.

Where baseline measurements and/or periodic measurements are available for comparison, definitive determinations regarding date ranges for exposure events can be established. However, even where baseline measurements were not made, a definitive determination regarding the occurrence of a past exposure (regardless of when) can still be made using example embodiments. Exposure statuses for military or civilians that were potentially targets of chemical weapons can therefore be determined over a range of possible agents, and within any suitable or practicable time period after a potential exposure event.

In some cases, as suggested above, it may be possible to determine some information about the type or nature of an exposure event or pattern based on test results. For example, level measurements coupled with information about the time since an exposure event may provide an indication of the magnitude of exposure. In some cases, the libraries may further include information indicative of level decay rates for various agents or metals, so that estimates can be generated based on available information regarding level and time for each individual agent or metal for which an exposure event is detected.

Thus, in some example embodiments, temporal information and/or type of exposure can be determined based on a regimen of testing. Moreover, given temporal information and level measurements, other information about the type of exposure and/or patterns of exposure may also be determinable. Example embodiments may therefore enable multiplex exposure detection to be accomplished for various metal ions (e.g., heavy metals) and chemical agents. Example embodiments may also be extended to provide further insights into autoimmune diseases and environmental exposures to improve public health and responses to humanitarian crises.

Figure 4:
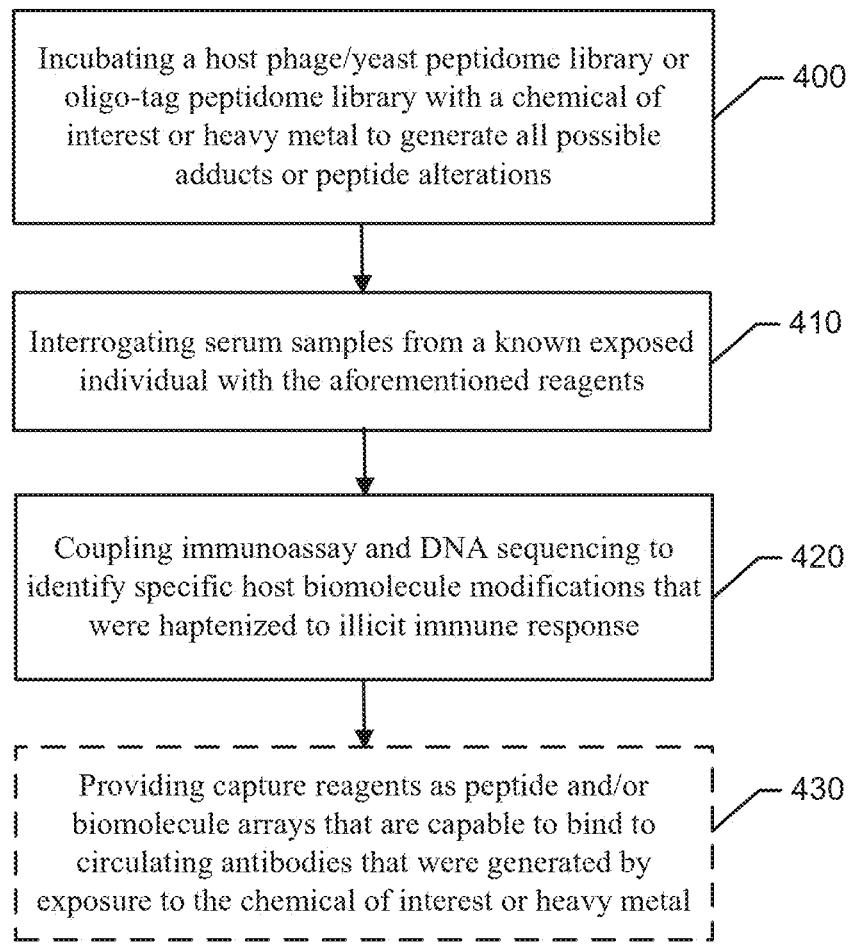
FIG. 4 illustrates a block diagram showing operations associated with a method for identifying possible host biomolecule modifications that illicit immune response following an exposure event to a chemical agent or heavy metal.

FIG. 4 illustrates a block diagram showing operations associated with a method for identifying possible host biomolecule modifications that illicit immune response following an exposure event to a chemical agent or heavy metal. As shown in FIG. 4, the method may include incubating a host phage/yeast peptidome library or oligo-tag peptidome library with a chemical of interest or heavy metal to generate all possible adducts or biomolecule conformational alterations at operation 400. The method may further include interrogating serum samples from a known exposed individual with the aforementioned reagents at operation 410. Thereafter, the method may include coupling immunoassay and DNA sequencing to identify specific host biomolecule modifications that were haptenized to illicit immune response at operation 420. An additional, optional modification to the method may include providing capture reagents as peptide and/or biomolecule arrays that are capable to bind to circulating antibodies that were generated by exposure to the chemical of interest or heavy metal at operation 430. Thus, as a result of the method of FIG. 4. Sufficient information may be determined to engage in the method of FIG. 3 with the corresponding identified capture reagents.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. An apparatus for determining past exposure to chemical agents or heavy metals, the apparatus comprising:
   a first capture material coated with a first capture reagent, the first capture reagent configured to bind to a first target antibody; wherein the first target antibody is an indicator associated with a first modified biomolecule associated with exposure to a first heavy metal, wherein the first heavy metal is lead;

a second capture material coated with a second capture reagent, the second capture reagent configured to bind to a second target antibody; wherein the second target antibody is an indicator associated with a second modified biomolecule associated with exposure to a second heavy metal;

a clinical sample associated with an individual;

a plurality of test cells including a first test cell housing a first mixture of the first capture material and the clinical sample, and a second test cell housing a second mixture of the second capture material and the clinical sample; and a detector configured to indicate (i) whether the first capture material formed a bond with the first target antibody and (ii) whether the second capture material formed a bond with the second target antibody.

2. The apparatus of claim 1, further comprising a third capture material coated with a third capture reagent, the third capture reagent configured to bind to a first protein adduct; wherein the first protein adduct is an indicator associated with exposure to a first chemical agent;

the plurality of test cells further comprising a third test cell housing a third mixture of the third capture material and the clinical sample; and the detector is further configured to indicate whether the third capture material formed a bond with the first protein adduct.

3. The apparatus of claim 2, further comprising a fourth capture material coated with a fourth capture reagent, the fourth capture reagent configured to bind to a second protein adduct; wherein the second protein adduct is an indicator associated with exposure to a second chemical agent;

the plurality of test cells further comprising a fourth test cell housing a fourth mixture of the fourth capture material and the clinical sample; and the detector is further configured to indicate whether the fourth capture material formed a bond with the second protein adduct.

4. An apparatus for determining past exposure to chemical agents or heavy metals, the apparatus comprising:

a first plurality of capture materials coated with a first plurality of respective capture reagents, the first plurality of capture materials being configured to bind to a first plurality of respective target antibodies; wherein the first plurality of respective target antibodies is an indicator associated with a first plurality of respective modified biomolecules associated with exposure to a first heavy metal, wherein the first heavy metal is lead;

a second plurality of capture materials coated with a second plurality of respective capture reagents, the second plurality of capture materials being configured to bind to a second plurality of respective target antibodies; wherein the second plurality of respective target antibodies is an indicator associated with a second plurality of respective modified biomolecules associated with exposure to a second heavy metal;

a clinical sample associated with an individual;

a first plurality of test cells housing a first plurality of respective mixtures of the first plurality of respective capture materials and the clinical sample;

a second plurality of test cells housing a second plurality of respective mixtures of the second plurality of respective capture materials and the clinical sample; and a detector configured to indicate whether any binding reactions occurred between (i) any of the first plurality of respective capture materials and the first plurality of respective target antibodies, and (ii) any of the second plurality of respective capture materials and the second plurality of respective target antibodies.

5. An apparatus for determining past exposure to chemical agents or heavy metals, the apparatus comprising:

a first capture material coated with a first capture reagent, the first capture reagent configured to bind to a first protein adduct; wherein the first protein adduct is an indicator associated with exposure to a first chemical agent;

a clinical sample associated with an individual;

at least one test cells housing a mixture of the first capture material and the clinical sample; and a detector configured to indicate whether the first capture material formed a bond with the first protein adduct.

6. The apparatus of claim 5, further comprising a second capture material coated with a second capture reagent, the second capture reagent configured to bind to a second protein adduct; wherein the second protein adduct is an indicator associated with exposure to a second chemical agent;

the at least one test cells comprises a plurality of test cells including a first test cell housing a first mixture of the first capture material and the clinical sample, and a second test cell housing a second mixture of the second capture material and the clinical sample; and the detector is further configured to indicate whether the second capture material formed a bond with the second protein adduct.

7. The apparatus of claim 5, wherein the first chemical agent is sarin gas.

8. The apparatus of claim 5, wherein the first chemical agent is mustard gas.

9. The apparatus of claim 6, wherein the first chemical agent is sarin gas and the second chemical agent is mustard gas.

* * * * *